(12) United States Patent
Hurwitz (10) Patent No.: US 7,780,972 B2
(45) Date of Patent: Aug. 24, 2010

(54) PET COLLAR WITH REPLACEABLE INSECTICIDE ELEMENT

(75) Inventor: Marni Markell Hurwitz, Far Hills, NJ (US)

(73) Assignee: IDIDIT, Inc., Far Hills, NJ (US)

( * ) Notice: Subject to any disclaimer, the term of this patent is extended or adjusted under 35 U.S.C. 154(b) by 792 days.

(21) Appl. No.: 11/482,391

(22) Filed: Jul. 7, 2006

(65) Prior Publication Data
US 2008/0008731 A1    Jan. 10, 2008

(51) Int. Cl.
*A01N 25/34* (2006.01)

(52) U.S. Cl. .................... 424/411; 424/764; 514/65; 514/341; 514/531

(58) Field of Classification Search ................... None
See application file for complete search history.

(56) References Cited

U.S. PATENT DOCUMENTS

| | | | |
|---|---|---|---|
| 2,219,569 A | 10/1940 | Vanderhoof | 119/860 |
| 3,978,820 A | 9/1976 | Drehman | 119/654 |
| 4,091,766 A | 5/1978 | Colliard | 359/518 |
| 4,158,051 A | 6/1979 | Greenberg et al. | 424/411 |
| 4,184,452 A | 1/1980 | Buzzell et al. | 119/654 |
| 4,218,991 A | 8/1980 | Cole | 119/654 |
| 4,879,117 A * | 11/1989 | Rombi | 424/411 |
| 4,900,876 A * | 2/1990 | Bushman et al. | 119/654 |
| 4,967,698 A | 11/1990 | Kennedy | 119/654 |
| 5,003,635 A * | 4/1991 | Peterson | 2/69 |
| 5,109,803 A | 5/1992 | Dunham et al. | 119/654 |
| 5,184,573 A | 2/1993 | Stevens, Jr. | 119/654 |
| 5,271,354 A | 12/1993 | Barnett | 119/654 |
| 5,555,848 A | 9/1996 | Trujillo et al. | 119/654 |
| 5,660,844 A | 8/1997 | Christie et al. | 424/411 |
| 5,970,921 A | 10/1999 | Fulton | 119/858 |
| 6,083,519 A | 7/2000 | Jeannin | 424/411 |
| D431,696 S | 10/2000 | Constantino | D30/152 |
| 6,372,242 B1 | 4/2002 | Gutierrez | 424/411 |
| 6,543,389 B2 | 4/2003 | Hedde | 119/654 |
| 6,685,954 B2 | 2/2004 | Jeannin | 424/405 |
| 7,117,659 B1 * | 10/2006 | Grogoza | 54/79.4 |
| 2005/0233900 A1 * | 10/2005 | Smith et al. | 502/407 |

OTHER PUBLICATIONS http://www.nrdc.org/health/effects/pets/execsum.asp.

* cited by examiner

*Primary Examiner*—Neil Levy
(74) *Attorney, Agent, or Firm*—Ernest D. Buff & Associates, LLC; Ernest D. Buff; Harry Anagnostopoulos

(57) ABSTRACT

A semi-flexible insecticide strip is removably attached to the belt of a pelt collar to regenerate a pest-killing medicament and increase its efficacy. The strip is secured to the belt surface that faces the animal skin or fur by attachment loops or edged retainers that are generally perpendicular to the length direction of the belt. Due to the geometry and elasticity of the semi-flexible insecticide strip, and its attachment method, the strip contacts the skin or fur of the animal despite movement of the pet collar when the animal is being exercised with a pet leash attached thereto. The contact effectively transfers the insecticide and kills ticks and fleas or retards development of mature flea adults. The insecticide is contained within a plurality of plastic pores of the insecticide strip or in a sponge affixed thereto.

19 Claims, 3 Drawing Sheets

PET COLLAR WITH REPLACEABLE INSECTICIDE ELEMENT

BACKGROUND OF THE INVENTION

1. Field of the Invention

The present invention relates to collars containing a chemical delivering element that protect pets against ticks or fleas; and, more particularly, to a collar wherein an insecticide composition is delivered against a pet's fur or skin and regenerated, when exhausted, by replacement of the chemical delivering element.

2. Description of the Prior Art

Pet collars with insecticide for killing or preventing hatching of eggs from fleas and ticks are well known in the art. The pesticides responsible for killing fleas and ticks interfere with the nervous system of the insect, blocking voltage sensitive sodium or chlorine channels and preventing nerve inhibition.

The oldest pesticide used is pyrethrins, which affects the nervous activity of the insect's nerve cells. Upon exposure to pyrethrins, the insect's flow of sodium is affected. Repeated and extended firing of nerve cells results in the death of the insect. The synergist most widely used with pyrethrins is piperonyl butoxide. Pyrethroids are synthetic pyrethrin compounds. They are made in a laboratory, and are not natural plant extracts. Common synthetic pyrethrins are allethrin, resmethrin, phenothrin, and permethrin. Permethrin and phenothrin are slower in action than the natural pyrethrins, but have a longer effect. Pyrethroids are less easily broken down than pyrethrin, so this makes their toxicity, though low, higher than that of pyrethrin. Adams Flea & Tick Collar uses Phenothrin Carbamates.

Next generation pesticides used in pet collars for killing ticks and fleas are organophosphates and organocarbamates. Organophosphates function by blocking nerve inhibition. When organophosphates are present, a nerve that is firing will continue to fire. This is accomplished by inhibiting acetylcholinesterase, an enzyme necessary for normal nerve function. Organophosphates should not be used on kittens or cats, though they are present in many commercial pet collars for cats. The seven organophosphates are chlorpyrifos, dichlorvos, phosmet, naled, tetrachlorvinphos, diazinon and malathion. These compounds are the active ingredients in dozens of pet products. A comprehensive list of EPA declared pesticides used in commercial flea and tick collar products is available at http://www.nrdc.org/health/effects/pets/execsum.asp. This list includes major pet pesticide brands, such as Alco, Americare, Beaphar, Double Duty, Ford's, Freedom Five, Happy Jack, Hartz, Hopkins, Kill-Ko, Protection, Rabon, Riverdale, Sergeant, Unicorn, Vet-Kem, Victory and Zema. For example, the insecticide Chlorpyrifos is contained in Hartz 330 day flea & tick collar for dogs, Happy Jack 3-X flea, tick and mange collar for cats and other pet collars. The insecticide Dichlorvos is used in Sergeant's Sentry Collar For Dogs, Sergeant's Sentry collar for cats and other pet collars. The insecticide Naled is present in Sergeant's Sentry IV flea & tick collar for dogs and cats. The insecticide Tetrachlorvinphos is used in Hartz 2 In 1 collar for dogs and cats. Diazinon is used in Protection 150 reflecting flea and tick collar for dogs and cats.

Insect growth regulators (IGRs) and insect development inhibitors (IDIs) are relatively new components of flea and tick products. Insect growth regulators include methoprene (Precor), fenoxycarb, and pyriproxyfen (Nylar). Insect growth inhibitors include lufenuron and diflubenzuron. Products containing IGRs and IDIs include Program, Sentinel, Bio Spot, Adams Flea and Tick Spray, Preventic Plus Flea and Tick Collar, and Frontline Plus. IGRs and IDIs differ from traditional flea product ingredients in that their main activity is against the immature forms of the flea. The IGRs mimic the juvenile growth hormone of fleas. A juvenile growth hormone is what keeps the fleas from developing into more mature forms. When the levels of juvenile growth hormone decrease, the larva form matures. The IGRs keep this development from occurring. The immature forms of the flea fail to molt and death occurs. The IDIs inhibit the synthesis of a substance called chitin. Chitin is necessary for the formation of the hard outside skin (cuticle) of the flea. If no chitin is present, no adult fleas are possible. The IGRs and IDIs do not kill the adult fleas. Accordingly, to be most effective, they should be used along with a product that does kill the adults (adulticide). If there is little risk of flea infestation, the IGRs and IDIs may be enough to prevent this occurrence. However, if flea problems already exist, or the risk is high, it is best to also use an adulticide in addition to IGRs and IDI. At present there are no effective IGRs or IDIs for ticks.

Amitraz is an ingredient that is used as a dip to treat demodectic mange. Amitraz has also been shown to be highly effective when used as an ingredient in canine tick collars. It has little or no effect on fleas, so is used in control of ticks only. Amitraz belongs to a group of drugs called formamidines and is an ingredient in Preventic Collars. Formamidines kill ticks by inhibiting their nerves Amitraz is not usable on cats.

Imidacloprid is another new insecticide, which is in yet a different class of chemicals. Commercial products Advantage, K9 Advantix contains imidacloprid. Imidacloprid is most commonly used as a once-a-month topical insecticide on dogs and cats to kill fleas. Imidacloprid is mixed with an oil carrier, and like Bio Spot for dogs containing permethrin, and Top Spot containing fipronil, the drug collects in the hair follicles from which it is slowly released. Imidacloprid has a wide margin of safety. Fipronil (Arylheterocycles) is the most commonly used product in this relatively new group of synthetic insecticides, such as Frontline Top Spot. The arylheterocycles (e.g. endosulfan and fipronil) are potent convulsants and insecticides that block the GABA-gated chloride channel, which leads to paralysis. Fipronil is most commonly used as a once-a-month topical insecticide on dogs and cats to kill fleas and ticks. Fipronil is generally mixed with an oil carrier, and like Bio Spot for Dogs containing permethrin, the drug collects in the hair follicles from which it is slowly released.

There are a number of insect control products that are not commonly used in pet collars. Selamectin (Revolution) kills parasites by blocking nerve signal transmissions. Revolution enters the bloodstream through the skin. It then stays in the bloodstream protecting against heartworm disease, passes into the gastrointestinal tract where it can kill certain intestinal parasites, and passes into the sebaceous glands and then onto the hair and skin providing protection against fleas and certain mites and ticks. Selamectin is a topical insecticide used for the treatment and prevention of fleas, ear mites, some internal parasites, and some types of mites and ticks; and the prevention of heartworm disease. Over 98% of fleas on the pet are killed within 36 hours of application. Once in contact with Revolution, fleas will not lay viable eggs. Nitenpyram (Capstar) is approved in dogs and cats to kill fleas. Nitenpyram interferes with the nerve conduction system of insects, blocking the nerve receptors. Nitenpyram in Capstar, an oral flea control product, is approved for use in dogs and cats over 4 weeks of age and 2 pounds of body weight. Nitenpyram starts killing adult fleas that are on the pet within 30 minutes. The peak effect after administering the medication is about 3 hours for the dog and 4 hours for the cat. It will not work for on-going control as the medication is out of the pet's system within 24 hours. Organochlorines are seldom seen on today's labels. The best known of the organochlorines is Lindane. Because of its side effects, Lindane is seldom used in over the counter products and would not be a choice for safe flea and tick control. Dioctyl sodium sulfosuccinate (docusate) and undecyclenic acid act by softening the waxy covering on fleas, ticks, lice, mites, and other insects, eventually affecting the internal organs and causing death of the insect.

Several prior art patents detail construction of pet collars in which the inside containing strip does not come in contact with the skin or fur of a cat or a dog in order to prevent severe skin irritation. These pet collars teach away from the disclosure of the subject invention, which makes intimate contact with the fur or skin of a cat or a dog. These prior art pet collars use insecticides of the old generation, which are toxic and constitute major skin irritants.

U.S. Pat. No. 2,219,569 to Vanderhoof discloses a germicidal animal collar. A leather collar is provided with leather pocket elements. A germicidal strip with stitched leather backing is tapered at its edges for insertion into the leather pockets, and is free to move as the pet collar is flexed. A central snap fastener also attaches the mid point of germicidal strip to the pet collar. The germicidal strip typically contains insect repellants; but does not contain compounds that kill or inhibit maturing of fleas and ticks. A snap attachment located at mid point indicates that the germicidal strip is not an easily replaceable element.

U.S. Pat. No. 3,978,820 to Drehman discloses a protective pet collar. The pet collar holds a strip of insecticide impregnated material around the neck of an animal. A strip of flexible material is provided with its longitudinal edges folded over towards its center so as to form a longitudinal holder. This longitudinal holder is capable of holding a strip of insecticide impregnated material. A plurality of openings are provided in each end of the holder. A lace, capable of passing through these openings, ties the ends of the holder together so as to secure the holder around the neck of the animal. The insecticide impregnated material does not contact the animal skin or fur.

U.S. Pat. No. 4,091,766 to Colliard discloses a pet collar. A neck embracing member of the collar has a tubular configuration and flexible characteristics. The neck embracing member facilitates the operable disposition of the collar around the neck of an animal. A reflective strip, insertable into the tubular member, has a reflective surface, which faces outwardly through a translucent sidewall of the embracing member. Light passing through the translucent sidewall of the embracing member is reflected by the reflective strip to signal the presence of the animal. A strip having characteristics for absorbing liquids is adhesively adhered to the outer surface of the tubular member for operable disposition in contact with the neck of the animal. The liquid impregnating the absorbent strip can either be an insecticide for inhibiting insect infestation, or a perfume for inhibiting animal odor and can be recharged by applying the liquid to the adhesively bonded absorbent strip. The absorbent strip is not replaceable, but is rather impregnated with a liquid periodically.

U.S. Pat. No. 4,158,051 to Greenberg, et al. discloses a pet collar. The pet collar is comprised of a synthetic resin such as polyvinyl chloride (PVC) having dispersed therein the insecticide naled (dimethyl 1,2-dibromo-2,2-dichloroethyl phosphate) and a substantially non-volatile carbamate. When naled insecticide, a substantially non-volatile carbamate insecticide and a surface porosity control component are incorporated in a resin matrix, the naled insecticide is released from the cured collar at a rate greater than from a cured collar containing only naled. This results in a more effective collar for the control of fleas and ticks on warm-blooded animals, particularly dogs and cats. This collar releases the naled and carbamate insecticide from the pores of a resin. There is no indication that the PVC resin strip with naled and carbamate insecticide is removably attached to a pet collar.

U.S. Pat. No. 4,184,452 to Buzzell, et al. discloses insect control collar with a replaceable chemical member. The animal collar has a member, which disperses a chemical to rid the animal of fleas and ticks. An elongate, porous netting member is secured along the surface of the collar body adjacent the animal to form an elongate pouch, which contains a chemically-impregnated plastic strip. The chemical-carrying member is periodically replaced for extended use of the collar. The chemical-carrying member is removably attached to the collar for easy replacement when the supply of chemical is exhausted. The chemically-impregnated member contains a chemical such as VAPONA (Trademark registered by Shell Chemical Co.) which is slowly released to rid the animals of fleas and ticks. The netting prevents direct contact between a pesticide chemical containing plastic strip and animal skin or fur. Only a vapor is delivered by the insect control collar.

U.S. Pat. No. 4,218,991 to Cole discloses a pet collar. A pair of resilient flanges extending lengthwise along the edges of the collar define a central, longitudinally extending channel. The flanges contain a longitudinal strip of pesticide treated material. This pesticide treated material is spaced apart from the skin or fur of the animal by the thickness and springiness of the flanges. Therefore effective transfer of the pesticide to ticks and fleas is not readily accomplished. Only the vapor of the pesticide has potential to be transferred to the ticks and fleas on the animal skin or fur.

U.S. Pat. No. 4,967,698 to Kennedy discloses an elastically resilient collar containing an insect-killing medicament. This elastically resilient collar is for application to a pet, such as a cat or dog, for the control of fleas and other insect pests that might infest the animal. Structurally, the collar comprises a helically wound spring like member forming an elongated void within which is deposited an appropriate medicament for killing insect pests. The helically wound structure may itself be formed from a synthetic resinous material having embedded therein the insect killing medicament. The elastically resilient collar does not have a replaceable insecticidal strip.

U.S. Pat. No. 5,109,803 to Dunham, et al. discloses a padded sleeve for a pet collar. This is a typical pet collar that is encased in a sleeve of a pliant, non-chafing padding that is in contact with a pet neck region. The sleeve is formed as an annular cylinder having a longitudinal overlapped portion. A plurality of releasable fasteners is distributed along the length to hold the overlapped flaps together to form the annular cylinder. Appropriate pesticides, deodorizing fragrances, and/or perfumes may be distributed along the interior length of the sleeve so as to be out of contact with the pet. The pesticide does not contact the skin or fur of the animal and at best only vapors of the pesticide are transmitted.

U.S. Pat. No. 5,184,573 to Stevens, Jr. discloses an Animal collar. This animal collar includes an elongate tubular member of open mesh polypropylene material having devices at its ends for securing the collar around the neck of an animal. A pesticide member is positioned within the elongate hollow mesh member. At least one of the openings of the mesh material is enlargeable, in which the pesticide member can be inserted or removed. Since a polypropylene mesh member is between the pesticide member and the skin or fur of the animal no direct contact is possible.

U.S. Pat. No. 5,271,354 to Barnett discloses an insect control collar for a pet. This is an annular collar comprising an elongated band having a top member and a bottom member. A support structure is carried between the top member and the bottom member with a space top member. The support structure defines side passages having side openings in communication with an insect controlling chemical, which is disposed within the collar. The chemical is delivered through side passages. No provision is made for replacement of the insecticide strip; the latter is permanently attached to the pet collar.

U.S. Pat. No. 5,555,848 to Trujillo, et al. discloses a pet/flea collar. This pet/flea collar includes a band with an exterior surface, an interior surface, a first end including a buckle, a second end having a buckle engaging portion with a plurality of holes formed in the band. The first and second ends are engaged using the holes to form a cylindrical pet collar. A ribbon of material has an exterior surface and an interior surface positionable on the interior surface of the band. The ribbon is permanently attached to the interior surface of the band, and forms a pocket on the band. The ribbon is an air permeable nylon mesh into which a strip of insecticide impregnated material is placed. There is no direct contact between the insecticide impregnated strip and the animal's skin or fur. Due to the air permeable nature of the nylon mesh, only vapors of the insecticide are delivered from the collar.

U.S. Pat. No. 5,660,844 to Christie, et al. discloses a collar to control arthropod infestations in animals. This collar contains a gel formulation of a wax and linear aliphatic hydrocarbon combination capable of the controlled release of an insecticide such as chlorpyrifos (DURSBAN) for the control of arthropods infesting animals. The gel is contained in an internal cavity polymeric reservoir, which is permeable to the active ingredient. The rate of release is proportional to chlorpyrifos concentration. The test collar described in example 6 of the '844 patent has a wall thickness of $\frac{1}{16}$ or $\frac{1}{32}$ inch and gel matrix with 20% Dursban™ pesticide. The gel containing reservoir is not a replaceable strip attached to a pet collar.

U.S. Pat. No. 5,970,921 to Fulton discloses a multi-function pet collar. This multi-function pet collar has a fastener for attaching the collar about an animal's neck. The collar conceals an extensible cover, which serves to protect the animal during inclement weather. This multi-layered cover includes an outer weather-proof layer of sheet plastic and an inner layer of cloth or thermal insulated material. The cover is secured about the animal's mid section with a tie strap that is passed through a waistband formed in the cover. The outer layer may also include light reflective strips positioned in predetermined locations to provide enhanced night visibility and protection from injury by motorists. The inner cloth layer may be provided with flea and parasite repellent strips to provide enhanced parasite protection while the animal is outdoors. The cover may be compactly folded and stored in a fabric pouch that is integrally formed with the collar. The inner cloth layer of the folded protective cover contains strips of parasite repellant, which is not a pesticide. The strips are not in the collar and are not removable.

U.S. Pat. No. 6,083,519 to Jeannin discloses N-phenylpyrazole-based anti-flea and anti-tick collar for cats and dogs. This collar device for a cat or dog is made of a matrix that incorporates from 0.1 to 40% by weight of N-phenylpyrazole-based substance, which is active against ectoparasites such as fleas and ticks. This active substance ensures more than 6 months of efficacy against fleas and more than 3 months of efficacy against ticks, the efficacy being maintained for several weeks even if the collar is lost. The active ingredient is incorporated in the matrix of the collar and is thus not removable or replaceable.

U.S. Pat. No. 6,372,242 to Gutierrez discloses a collar containing a novel gel formulation to control arthropod infestation of animals. The collar is capable of the controlled, sustained release of an effective amount of an active ingredient that can protect an animal against arthropod pests. It comprises a reservoir containing a novel gel formulation containing a fatty acid, an organic solvent which is a linear aliphatic ester, a silicone-based fluid, or a combination thereof, and an active ingredient that can protect the animal against one or more arthropod pests. The fatty acid is selected from the group of fatty acids having an unbranched hydrocarbon chain from about $C_{15}$ to about $C_{17}$ in length. The active ingredient is selected from the group consisting of lindane, methoxychlor, permethrin, cypermethrin, dichlorvos, diazinon, chlorfenvinphos, bendiocarb, amitraz, chlorpyrifos, deltamethrin, sevin, and a combination thereof. The gel is slowly released from a reservoir that is part of the pet collar and is not removable or replaceable.

U.S. Pat. No. 6,543,389 to Hedde discloses an insecticidal pet collar. The insecticide in the pet collar is amitraz, or a pharmaceutically acceptable salt thereof. Atipamezole is incorporated in the matrix of the collar. No provision is made for a removable strip that contains the insecticide.

U.S. Pat. No. 6,685,954 to Jeannin discloses an insecticidal combination to control mammal fleas and, in particular, fleas on cats and dogs. Local application to the skin of an animal with a composition containing insecticide of 1-N-arylpyrazole (fipronil) and a compound of IGR (insect growth regulator) type in a fluid vehicle provides control of fleas on small mammals. This topical application does not involve use of a pet collar or a replaceable insecticide strip.

Notwithstanding the efforts of prior art workers to construct an insecticide containing pet collar, there remains a need in the art for a pet collar wherein only the insecticide containing element is replaced. Recent developments in insecticide chemical compositions and insect growth inhibiting compositions led to introduction of pest-killing compounds that can be brought into contact with the fur or skin of an animal without causing irritation or skin damage. Accordingly, there exists a need in the art for a robust collar wherein the pesticide/insecticide containing element can be replaced without discarding the collar. Also needed is a collar in which the insecticide containing element is maintained in direct contact with the animal skin or fur for effectiveness of flea and tick control during attachment of the pet collar to a leash used for pet walking or other activities which involve pet movement.

SUMMARY OF THE INVENTION

The present invention provides a pet collar containing a pest killing medicament which is readily regenerated by replacement of an insecticide containing element. A medicament comprising an insecticide chemical composition and/or an insect growth inhibiting composition is brought into direct contact with the fur or skin of an animal without causing irritation or skin damage. The collar is so robust that the pesticide/insecticide containing element can be replaced many times without discarding the collar. Direct contact between the insecticide containing element and the animal's skin or fur is reliably maintained despite attachment of the pet collar to a leash used for pet walking or other activities that involve pet movement, thereby enhancing efficacy of the collar for flea and tick control.

Generally stated, the pet collar comprises a belt with a buckle on one side, a free end on the other side and an attachment means, such as apertures disposed longitudinally within the central portion of the belt, or a quick release clasp mechanism, for securing the collar in a closed loop configuration. The belt portion of the collar is provided with a plurality of loops and/or edge retainers for attaching thereto a replaceable semi-flexible insecticide strip. The attachment loops and edge retainers are generally perpendicular to the length of the collar's belt portion. Advantageously, an insecticide strip inserted within the attachment loops contacts the animal skin or fur directly when the pet collar is secured to the neck of an animal such as a cat or a dog. The replaceable semi-flexible insecticide containing element has sufficient rigidity to facilitate its insertion through the loops provided by the belt of the pet collar. Once inserted, the insecticide containing element stays in place without buckling or forming wrinkles of the type experienced with use of a linen or cotton pad. The replaceable, semi-flexible insecticide containing element is retained securely in place by the loops, causing the portions of the element between the loops to contact the animal's fur or skin. Advantageously, this contact is reliably maintained even when the pet collar encounters strong tensile forces from the tugging action generated during periods when the animal is being walked by the owner using a leash attached to the pet collar.

In an alternate embodiment, the replaceable semi-rigid insecticide strip is retained by a pair of edge retainers. A plurality of pairs of edge retainers are distributed along the length of the belt of the pet collar. Smaller lengths of replaceable semi-flexible insecticide strips are retained by each pair of edge retainers. The insertion of these strips is easy since the belt of the pet collar may be opened at the buckle and flexed in the opposite direction, as compared to normal in use position. In this condition, the distance between the edge retainers is increased and the replaceable semi-flexible insecticide strip may be easily inserted. In the in-use position, the semi-flexible insecticide strips are securely held within the edge retainer and the portion of the semi-flexible insecticide strip directly contacts the skin or fur of the animal. The movement of the collar does not displace the semi-flexible insecticide strip from the animal's skin or hair owing to the elastic properties of the semi-flexible strip.

The pet collar housing has a buckle and a plurality of holes for engagement therewith. A plurality of attachment loops and/or edge retainers capture a replaceable semi-rigid insecticidal strip. The loops alone may attach a semi-flexible insecticidal strip to the belt of the pet collar on its skin or fur contacting face. Edge retainers may be used in conjunction with attachment loops to secure the edges of the long length continuous semi-flexible insecticidal strips. The semi-flexible insecticide strip contacts the animal skin or fur in the space between the attachment loops. Due to the elastic properties of the semi-rigid insecticidal strip, the contact between the semi-flexible insecticidal strip and the animal skin or fur is maintained even when the animal or pet collar is moved. In the second embodiment, several pairs of L shaped edge retainers are provided on the belt and carry smaller length semi-flexible insecticide strips. Typically, the length of the semi-flexible insecticide strips is slightly smaller than the capture length of the edge retainers, which is the distance between the insides of the L shaped edge retainers. This length is generally larger than the distance between the interior retainer portions, between the legs of the L shaped retainers. Hence, the semi-flexible insecticide is completely retained within the edge retainers. With this arrangement, the semi-flexible insecticide strip contacts the skin or fur of the animal between the edge retainers. Optionally, each pair of edge retainer may be provided with a closure edge parallel to the length of the belt on opposite sides to prevent sliding of the semi-flexible insecticide strip within the edge retainers in a direction perpendicular to the length of the belt.

The semi-flexible insecticide strip may be fabricated from a polymeric strip. The polymer used in the strip may be poly vinyl chloride, high-density polyethylene, polyolefin or other suitable polymers. The only requirement is that the polymer strip be semi-flexible, which facilitates its insertion into the attachment loops and promotes retention thereof by the edge retainers. In addition, the insecticide strip should have sufficient elastic properties to press against the skin or fur of the animal when attached to the belt of the pet collar. The polymeric sheet may be provided with porosity to contain the insecticide composition. Alternatively, a sponge like element may be bonded on one side to the semi-flexible polymeric strip, which is soaked in the insecticide. In the case where a sponge is bonded to the semi-flexible polymeric strip, the insecticide containing sponge faces the skin or fur of the animal. As a still further alternative the semi-flexible polymeric strip can be coated on one or both sides with a thin film which is readily ruptured by pulling firmly on opposite ends of the strip. Upon being ruptured, the film separates, permitting the insecticide ingredients to become activated. An insecticide ingredient particularly well suited for use with this embodiment comprises tetrachlorvinphos, (CAS#22248-79-9), which is sold by Hartz Mountain Corporation, Secaucus, N.J. This feature protects the user by restricting contact with the insecticide contained by the strip.

The insecticide used in the semi-flexible polymeric strip or attached sponge may be selected from a variety of currently available insecticidal compositions, including those from pyrethrins group, organophosphate group, Imidacloprid, Arylheterocycles and insect growth regulators (IGR) or insect development inhibitors (IDI) or combinations thereof. Formamidines (Amitraz), which are effective against ticks may be combined in the composition. Organophosphates include chlorpyrifos, dichlorvos, phosmet, naled, tetrachlorvinphos, diazinon, malathion. Insect growth regulators (IGR) include methoprene (Precor), fenoxycarb, and pyriproxyfen (Nylar). Insect development inhibitors (IDI) include lufenuron and diflubenzuron. Both IGR and IDI to control development of adult fleas and therefore control flea population. These compositions are readily soluble in organic fatty acids fatty acids having an unbranched hydrocarbon chain from about $C_{15}$ to about $C_{17}$ in length and organic solvents, which is a linear aliphatic ester. The imidacloprid or arylheterocycles (e.g. endosulfan and fipronil), which produce convulsion in insects and are carried at the hair follicles of the animal may be dissolved in a similar manner. Any combination of these insecticide compositions in a solvent or fatty acid base is incorporated in the semi-flexible insecticide strip or on the sponge attached to a semi-flexible polymeric strip. Due to the dilution of the insecticide present, the composition is not an irritant and is safe to handle. Due to the large overall length and width of the semi-flexible insecticide strip a large area of the animal is treated targeting a larger number of ticks and fleas.

When the semi-flexible insecticide strip has passed its lifetime, it may be readily replaced with a new strip without discarding the pet collar. The semi-flexible insecticide strip or the semi-flexible plastic strip with a sponge soaked in insecticide may be marketed in a sealed pouch with a ready-to-peel closure member attached to the insecticide containing face. The user inserts the semi-flexible insecticide strip into the attachment loops and proceeds to peel away the protective closure. This procedure limits the human contact of the insecticide. At any case, due to the dilution of the insecticide in the semi-flexible insecticide strip, the insecticide concentration is significantly reduced.

In the case of a pair of edge retainers holding the semi-flexible insecticidal strip, the procedure involves opening out the pet collar by loosening the buckle to expose the skin or fur contacting face of the pet collar. The belt of the pet collar is folded away from the use direction, exposing the pair of edge retainers on a convex surface. This opens out the distance between the edge retainers of the pair and the semi-flexible insecticide strip can be easily removed. A new semi-flexible insecticide strip with fresh insecticide is placed between the edge retainers. On the other hand, the semi-flexible insecticide strip may be slid along the width direction of the belt and a new strip inserted. The pair of edge retainers may be provided with end closure elements on opposing sides to prevent this sliding action. In this case, the convex surface method is effective to remove used strips and inset new strips. Advantageously, with use of the quick-release attachment means, the pet collar is readily attached to the neck of the pet. This embodiment is particularly well suited for use with household pets. When combined with a break away component, the quick-release embodiment is particularly well suited for cat collars.

BRIEF DESCRIPTION OF THE DRAWING

The invention will be more fully understood and further advantages will become apparent when reference is had to the following detailed description of the preferred embodiments of the invention and the accompanying drawings, in which.

DETAILED DESCRIPTION OF THE INVENTION

The present invention provides a pet collar, which has provisions for attaching a replaceable semi-flexible insecticide strip. The semi-flexible insecticide strip is brought to bear on the skin or fur of the animal at locations between attachment locations, enlarging the contact area and thereby increasing the efficiency of the strip for insecticide killing or preventing development of fleas or ticks. Due to the elasticity of the semi-flexible insecticide strip, the contact with the animal skin or fur is intimately maintained even when the pet collar is moved by activity such as exercising or walking a pet using a pet leash attached to the pet collar.

The pet collar has a belt, which is made from a variety of materials including nylon, polyester leather or other suitable material. The belt material may be treated with a waterproofing compound to limit the amount of water reaching the semi-flexible insecticide strip attached to the belt by attachment means. The nylon or polyester belt may be interwoven with reflective fibers to enhance the visibility of the pet collar during nighttime hours. The belt may be treated with antimicrobial agents to prevent odor formation since it is used many times by replacing the removable semi-flexible insecticide strips.

The attachment means of connecting the semi-flexible insecticide strip to the belt of the pet collar includes use of attachment loops generally oriented perpendicular to the length direction of the pet collar belt. The semi-flexible insecticide strip is inserted through the loops after removing an exhausted semi-flexible insecticide strip. Optionally, the ends of this semi-flexible insecticide strip may be contained in an edge retainer, which is also oriented perpendicular to the pet collar belt length dimension. In this arrangement, the semi-flexible insecticide strip is retained in all directions. The movement along the belt direction is stopped by the edge retainers and its movement perpendicular to the belt direction is stopped by the attachment loops. The tension of the pet collar and the elasticity of the semi-flexible insecticide strip create forces that serve collectively to retain the strip in place against the skin or fur of the animal.

The second attachment means uses a plurality of paired L shaped edge retainers which face each other, so that the leg of the L functions to retain the semi-flexible insecticide strip. There are key length requirements in this arrangement. First, the length of the semi-flexible insecticide strip should be slightly smaller than the inner length between L shaped edge retainers that face each other. The distance between the legs of the L shape retainers must be smaller than the length of the semi-flexible insecticide strip so that it is held in place. When the pet collar buckle is opened out and flexed in a direction when the edge retainers are on a convex face, the distance between the edge retainers is increased and at this time, the semi-flexible insecticide strips can be easily removed and fresh new semi-flexible insecticide strips may be inserted into the belt of the pet collar. Alternatively, the semi-flexible insecticide strips may be slid out along the width of the belt and new ones inserted in the same manner. In an alternate embodiment, the movement of the semi-flexible insecticide strip along the width of the belt may be completely prevented by providing closure edges to the pair of opposing L shaped edge retainers, securing the movement in opposite directions.

The semi-flexible insecticide strip is made from a polymeric material. Polymers suitable for the semi-flexible insecticide strip include, but are not limited to poly vinyl chloride, polyethylene, poly olefin and others. In one embodiment, the polymeric strip has a porous structure filled with insecticide composed of a solution in a solvent that comprises a linear aliphatic ester or a fatty acid. In a second embodiment, a sponge is attached to a solid polymeric strip, which carries the insecticide solution in a solvent or a fatty acids having an unbranched hydrocarbon chain from about $C_{15}$ to about $C_{17}$ in length. The insecticide may be selected from a variety of currently available compositions, comprising those from the pyrethrins group, the organophosphate group, Imidacloprid, Arylheterocycles and insect growth regulators (IGR) or insect development inhibitors (IDI) or combinations thereof. Formamidines (Amitraz), which are effective against ticks may be combined in the composition. Organophosphates include chlorpyrifos, dichlorvos, phosmet, naled, tetrachlorvinphos, diazinon, malathion. Insect growth regulators (IGR) include methoprene (Precor), fenoxycarb, and pyriproxyfen (Nylar). Insect development inhibitors (IDI) include lufenuron and diflubenzuron. Both IGR and IDI prevent development of adult fleas and therefore control flea population. These compositions are readily soluble in organic fatty acids having an unbranched hydrocarbon chain from about $C_{15}$ to about $C_{17}$ in length and organic solvents, which is a linear aliphatic ester. The imidacloprid or arylheterocycles (e.g. endosulfan and fipronil), which produce convulsion in insects and are carried at the hair follicles of the animal, may be dissolved in a similar manner and incorporated in the semi-flexible insecticide strip or on the sponge attached to a semi-flexible polymeric strip. Due to the dilution of the insecticide present, the composition is not an irritant and is safe to handle. Due to geometry and elasticity of the semi-flexible insecticide strip, and the looped arrangement of the attaching means, a large area of the animal is treated, targeting a larger number of ticks and fleas and increasing the efficacy of the insecticide containing strip.

Figure 1A:
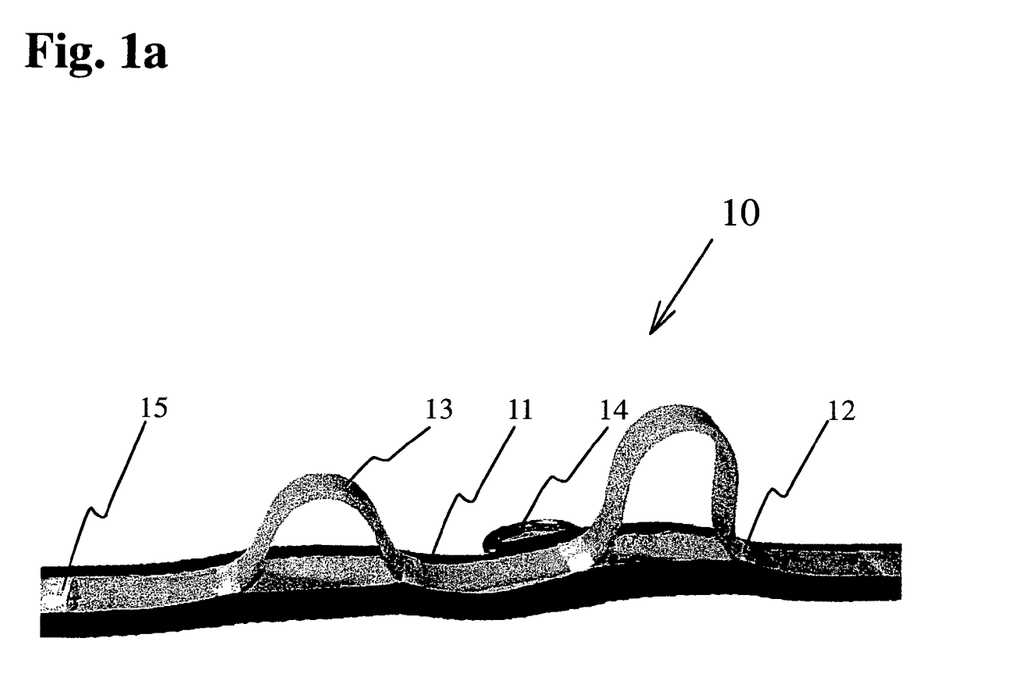
FIG. 1a is a photograph of a pet collar having attachment loops into which a semi-flexible insecticide strip is being inserted

FIG. 1a shows generally at 10 a photograph depicting a pet collar with a belt 11 attached, to which are attachment loops 12. A semi-flexible insecticide strip 13 is being inserted through the loops on the animal skin or fur contacting face of the pet collar. The end of the semi-flexible insect strip may be contained in an edge retainer 15, as shown. The pet collar has a ring 14 for attaching a pet leash thereto.

Figure 1B:
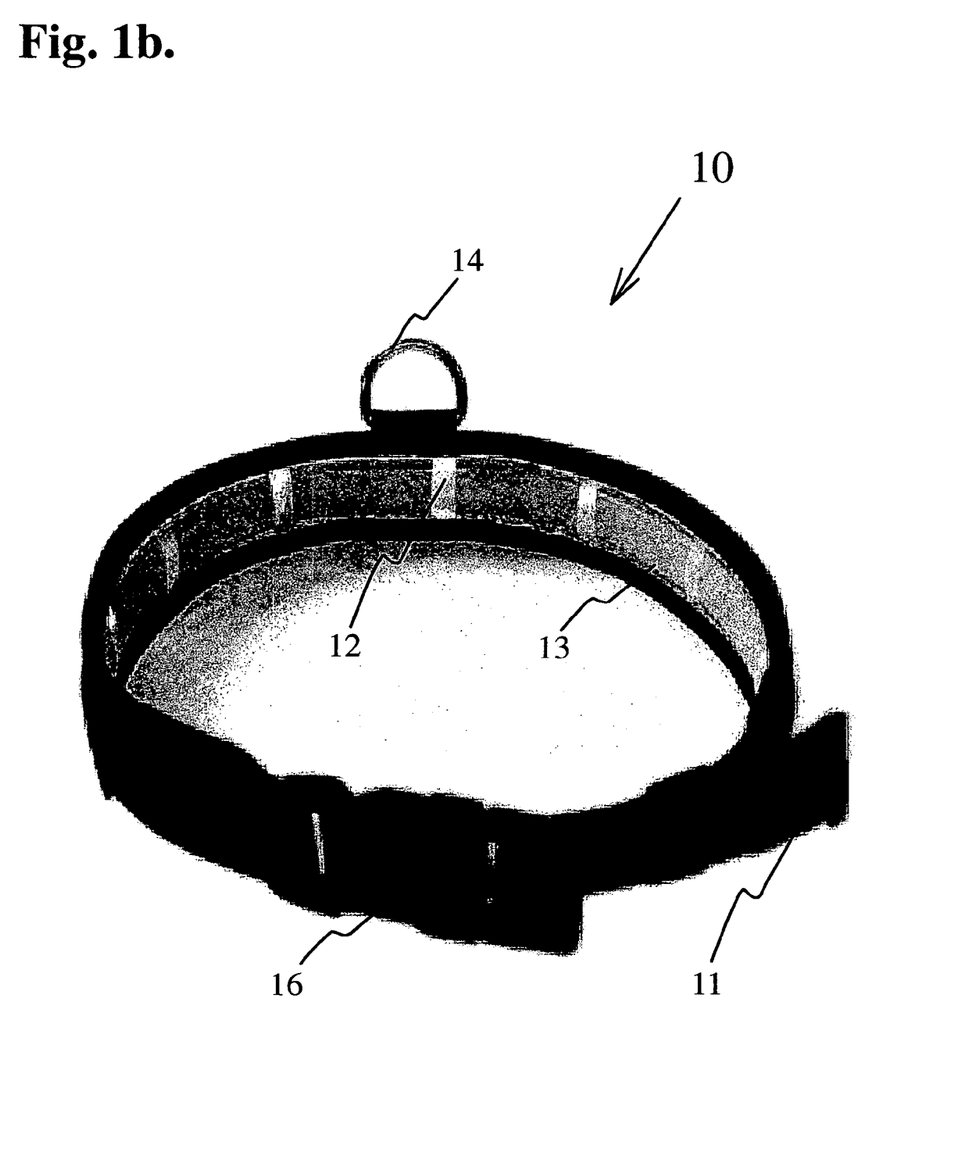
FIG. 1b is a photograph of a pet collar having attachment loops, with a semi-flexible insecticide strip completely inserted.

FIG. 1b shows generally at 10 a photograph depicting the pet collar after assembly of the semi-flexible insect strip 13 into attachment loops 12 has been completed. The pet collar 10 has a buckle element 16 for attaching the collar to the neck of an animal. The ring 14 is provided for attaching a pet leash to the pet collar.

Figure 2A:
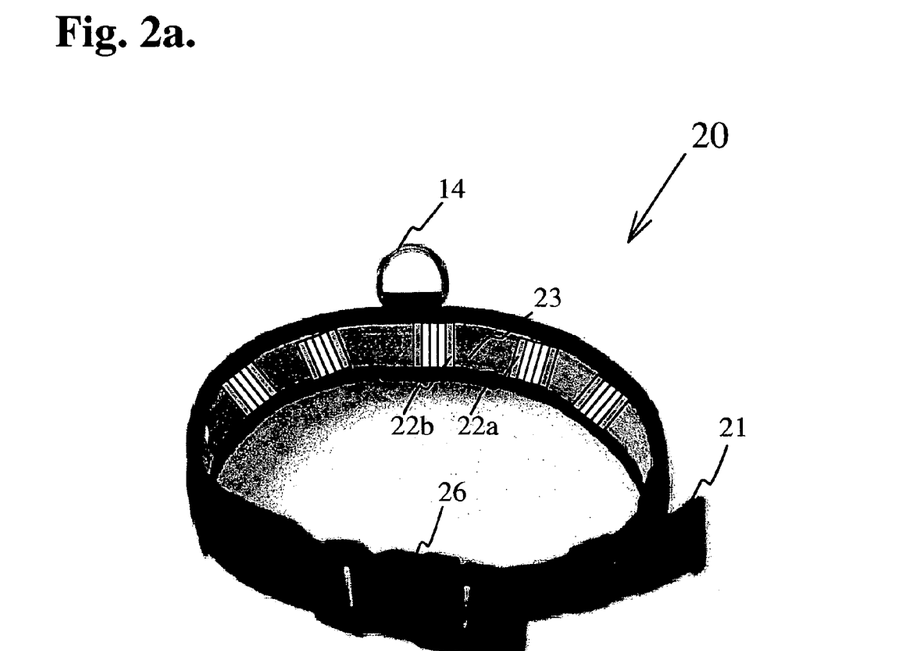
FIG. 2a is a photograph of the second embodiment of the invention depicting a pet collar having plurality of edge retainers with semi-flexible insecticide strips.

FIG. 2a shows generally at 20 a photograph depicting the second embodiment of the invention, wherein several semi-flexible insecticide strips 23 are individually held in place by a plurality of edge retainer pairs 22a and 22b.

Figure 2B:
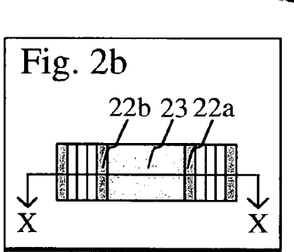
FIG. 2b is a schematic diagram of the semi-flexible insecticide strip held by a pair of edge retainers.
Figure 2C:
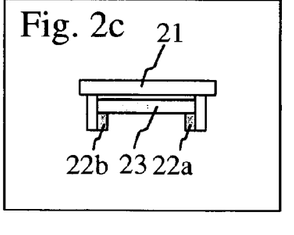
FIG. 2c is a cross sectional view of the pet collar of FIG. 2b taken along the line XX, showing the details of the edge retainers and the semi-flexible insecticide strip.

FIG. 2b shows schematically details concerning the relationship between the semi-flexible insecticide strip 23 and a single pair of edge retainers 22a and 22b. A cross section of the arrangement, taken along the line XX, is shown in FIG. 2c. The belt 21 is attached to L shaped edge retainer 22a. A second edge retainer 22a, which is an inverted L, is attached to the belt at a fixed distance. The semi-flexible insecticide strip is placed as shown with the legs of the L shaped edge retainers 22a and 22b retaining the strip.

Figure 2D:
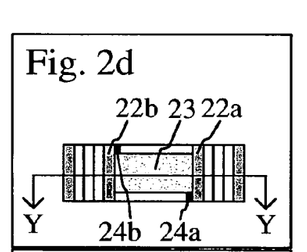
FIG. 2d is a schematic diagram depicting details of a pair of edge retainers having edge closure elements to prevent the slipping out of the semi-flexible insecticide strip.
Figure 2E:
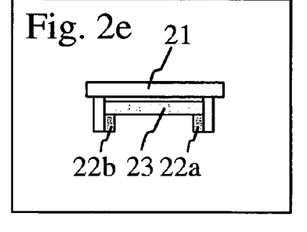
FIG. 2e is a cross sectional view of the pet collar of FIG. 2d, taken along the line YY, showing the details of the edge retainers and the relative dimensions of the semi-flexible insecticide strip.

FIGS. 2d and 2e are similar to the embodiment detailed in FIGS. 2b and 2c, except that the lateral edge of the semi-flexible insecticidal strip is supported by two closure edge projections 24a and 24b. Note that the closure edges are in different locations so that the semi-flexible insecticide strip may not slip away from the edge retainers.

The key features of the pet collar having a replaceable insecticide element include, in combination, the components set forth below:

1. a belt with buckle and holes or, preferably, a quick release attachment means, for securing the pet collar to the neck of an animal;
2. the belt being composed of a variety of materials including leather, nylon, polyester and the like;
3. optionally the nylon or polyester belt being woven with a reflective fiber for nighttime illumination of the pet collar, facilitating recognition of the pet's presence;
4. optionally the belt being treated with a water repellant composition to protect the semi-flexible insecticide strip.
5. optionally the belt being treated with an antimicrobial composition to combat odor development, facilitating repeated use of the belt and regeneration of the pest-killing medicament by replacement of the semi-flexible insecticide strip associated therewith;
6. said belt having an attachment means for attaching the semi-flexible insecticide strip on the face of the belt that is appointed for contact with the skin or fur of the animal;
7. the semi-flexible insecticide strip containing in the pores of a polymeric strip or in a sponge bonded to a solid plastic strip an insecticide composition that includes at least one member from the pyrethrins group or the organophosphate group, imidacloprid, arylheterocycles and an insect growth regulator (IGR) or an insect development inhibitor (IDI), or combinations thereof, dissolved in solvents or fatty acids;
8. the attachment means including a plurality of loops that are perpendicular to the length dimension of the belt for receiving a long-length insecticide strip;
9. optionally the ends of the long-length semi-flexible insecticide strip being contained in an edge retainer;
10. the attachment means including a plurality of short-length, semi-flexible insecticide strips held in the belt of the pet collar by a plurality of pairs of edge retainers disposed along the width direction of the belt;
11. each pair of the edge retainers comprising two opposing L shaped edge retainers attached to the belt with the legs of the L shape supporting the insecticide strip; and
12. Optionally, the edge retainers being provided with closure edge projections to prevent lateral displacement of the insecticide strip along the width of the belt;

whereby the semi-flexible insecticide strip maintains contact with the skin or fur of an animal owing to is elasticity, transferring liquid or vapor insecticide to ticks and fleas that are resident on the animal, to thereby kill or retard growth of the tick and flea population.

Having thus described the invention in rather full detail, it will be understood that such detail need not be strictly adhered to, but that additional changes and modifications may suggest themselves to one skilled in the art. For example, the insecticide containing strip can be replaced with a semi-flexible strip comprising a chemical that simulates natural calming pheromones, which help sooth a dog in stressful situations. One such chemical comprises about 2% by weight D.A.P. (a registered trademark of Ceva Sante Animale), the balance being isopropanol. The use of a semiflexible strip containing such a chemical has been proven to reduce or completely stop stress-related behavior in dogs, including barking, urination and defecation, whimpering and whining, anxiety, and chewing. It is also helpful in reducing stress from flee infestation in household pets. In yet another embodiment, the insecticide containing strip can be replaced with a strip that is impregnated with mosquito repellant. Or, the insecticide containing strip can additionally be treated to provide a mosquito repelling function. In yet another embodiment, the insecticide containing strip can be accompanied by a collar of the type described herein, but which is, itself, treated with the mosquito repellant composition. One type of mosquito repelling composition that has been found suitable for this purpose is sold under the tradename "Cutter" by Spectrum, a division of United Industries Corporation. The Cutter mosquito repellant contains as the active ingredient approximately 7% Picardin, as well as other ingredients. Another suitable composition is sold under the tradename "Sargents". This composition contains, as the active ingredients approximately 45% Permethrin and 5% Pyriproxyfen, together with other inert ingredients. Each of these modifications is intended to fall within the scope of the invention as defined by the subjoined claims.

What is claimed is:

1. A pet collar for control of fleas and ticks, comprising:
   a. a belt having a length direction and a width direction;
   b. said belt being provided with a pet collar attachment means adapted to attach said pet collar to the neck of an animal;
   c. the belt having a face that contacts the skin or fur of said animal, said face being provided with insecticide strip attachment means that are generally perpendicular to the width direction of the belt for receiving a removable semi-flexible insecticide strip;
   d. said removable semi-flexible insecticidal strip containing an insecticidal composition as a solvent solution or a solution in a fatty acid, or combinations thereof, in a plurality of pores of a polymeric strip or in the pores of a sponge bonded to a polymeric strip;
   e. said insecticidal composition being a member selected from pyrethrins group, imidacloprid and combinations thereof;
   f. said belt is treated with an antimicrobial agent to prevent odor development;
   g. said plastic of said semi-flexible insecticide strip is poly vinyl chloride, high density polyethylene or polyolefin;
   h. said belt is treated with a water repellant composition to protect said semi-flexible insecticide strip;
   whereby said semi-flexible insecticide strip maintains contact with the skin or fur of an animal due to is elasticity, transferring liquid or vapor insecticide to ticks and fleas and thereby killing or retarding growth of said animal's tick and flea population.

2. A pet collar as recited by claim 1, wherein the pet collar attachment means includes a buckle and a plurality of holes in said belt.

3. A pet collar as recited by claim 1, wherein the insecticide strip collar attachment means includes a plurality of attachment loops permanently attached to an animal skin or fur contacting face of said belt.

4. A pet collar as recited by claim 1, wherein the insecticide strip collar attachment means includes a plurality of pairs of edge retainers attached to an animal skin or fur contacting face of said belt.

5. A pet collar as recited by claim 3, wherein the attachment loops carry a single long length semi-flexible insecticide strip.

6. A pet collar as recited by claim 4, wherein a pair of edge retainers of said plurality of pairs of edge retainers carries a short length semi-flexible insecticide strip.

7. A pet collar as recited by claim 6, wherein said pair of edge retainers comprise two opposing elements having an L shaped cross section, the leg of the L shape supporting said short length semi-flexible insecticide strip.

8. A pet collar as recited by claim 7, wherein said pair of edge retainers is provided with opposing end closures to prevent displacement of said short length insecticide strip along the width direction of the belt of the pet collar.

9. A pet collar as recited by claim 1, wherein said belt is made from leather, nylon, polyester or polyolefin.

10. A pet collar as recited in claim 9, wherein said nylon, polyester or polyolefin belt includes a plurality of reflective fibers for nighttime illumination said pet collar.

11. A pet collar for control of fleas and ticks, comprising:
   a. a belt having a length direction and a width direction;
   b. said belt being provided with a pet collar attachment means adapted to attach said pet collar to the neck of an animal;
   c. the belt having a face that contacts the skin or fur of said animal, said face being provided with insecticide strip attachment means that are generally perpendicular to the width direction of the belt for receiving a removable semi-flexible insecticide strip;
   d. said removable semi-flexible insecticidal strip containing an insecticidal composition as a solvent solution or a solution in a fatty acid, or combinations thereof, in a plurality of pores of a polymeric strip or in the pores of a sponge bonded to a polymeric strip;
   e. said insecticidal composition being a member selected from pyrethrins group, imidacloprid and combinations thereof;
   f. said belt is made from nylon, polyester or polyolefin;
   g. said belt includes a plurality of reflective fibers for nighttime illumination said pet collar;
   h. said plastic of said semi-flexible insecticide strip is poly vinyl chloride, high density polyethylene or polyolefin;
   i. said belt is treated with a water repellant composition to protect said semi-flexible insecticide strip;
   whereby said semi-flexible insecticide strip maintains contact with the skin or fur of an animal due to is elasticity, transferring liquid or vapor insecticide to ticks and fleas and thereby killing or retarding growth of said animal's tick and flea population.

12. A pet collar as recited by claim 11, wherein the pet collar attachment means includes a buckle and a plurality of holes in said belt.

13. A pet collar as recited by claim 11, wherein the insecticide strip collar attachment means includes a plurality of attachment loops permanently attached to an animal skin or fur contacting face of said belt.

14. A pet collar as recited by claim 11, wherein the insecticide strip collar attachment means includes a plurality of pairs of edge retainers attached to an animal skin or fur contacting face of said belt.

15. A pet collar as recited by claim 13, wherein the attachment loops carry a single long length semi-flexible insecticide strip.

16. A pet collar as recited by claim 14, wherein a pair of edge retainers of said plurality of pairs of edge retainers carries a short length semi-flexible insecticide strip.

17. A pet collar as recited by claim 16, wherein said pair of edge retainers comprise two opposing elements having an L shaped cross section, the leg of the L shape supporting said short length semi-flexible insecticide strip.

18. A pet collar as recited by claim 17, wherein said pair of edge retainers is provided with opposing end closures to prevent displacement of said short length insecticide strip along the width direction of the belt of the pet collar.

19. A pet collar as recited in claim 11, wherein said belt is treated with an antimicrobial agent to prevent odor development.

* * * * *